United States Patent
Keusenkothen et al.

(10) Patent No.: US 9,714,386 B2
(45) Date of Patent: Jul. 25, 2017

(54) PRODUCTION OF XYLENES FROM SYNGAS

(71) Applicant: ExxonMobil Chemical Patents Inc., Baytown, TX (US)

(72) Inventors: Paul F. Keusenkothen, Houston, TX (US); Juan D. Henao, Houston, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 67 days.

(21) Appl. No.: 14/753,692

(22) Filed: Jun. 29, 2015

(65) Prior Publication Data

US 2016/0024392 A1 Jan. 28, 2016

Related U.S. Application Data

(60) Provisional application No. 62/028,486, filed on Jul. 24, 2014.

(51) Int. Cl.

| | | |
|---|---|---|
| *C10G 2/00* | (2006.01) | |
| *B01J 35/00* | (2006.01) | |
| *B01J 29/48* | (2006.01) | |
| *B01J 29/42* | (2006.01) | |
| *B01J 29/40* | (2006.01) | |
| *B01J 29/076* | (2006.01) | |
| *B01J 29/064* | (2006.01) | |
| *B01J 23/12* | (2006.01) | |
| *B01J 23/10* | (2006.01) | |
| *B01J 23/06* | (2006.01) | |
| *B01J 21/06* | (2006.01) | |
| *C10G 29/20* | (2006.01) | |
| *C10G 29/22* | (2006.01) | |
| *C10G 45/58* | (2006.01) | |
| *C07C 1/04* | (2006.01) | |
| *C07C 2/86* | (2006.01) | |
| *C07C 5/27* | (2006.01) | |
| *C07C 6/12* | (2006.01) | |

(52) U.S. Cl.
CPC ............ *C10G 2/334* (2013.01); *B01J 21/066* (2013.01); *B01J 23/06* (2013.01); *B01J 23/10* (2013.01); *B01J 23/12* (2013.01); *B01J 29/064* (2013.01); *B01J 29/076* (2013.01); *B01J 29/405* (2013.01); *B01J 29/42* (2013.01); *B01J 29/48* (2013.01); *B01J 35/0006* (2013.01); *C07C 1/0425* (2013.01); *C07C 1/0485* (2013.01); *C07C 2/864* (2013.01); *C07C 5/2732* (2013.01); *C07C 6/126* (2013.01); *C10G 2/331* (2013.01); *C10G 29/205* (2013.01); *C10G 29/22* (2013.01); *C10G 45/58* (2013.01); *C07C 2529/40* (2013.01); *C10G 2400/30* (2013.01); *Y02P 20/52* (2015.11)

(58) Field of Classification Search
CPC ........ C10G 2/334; C10G 45/58; C10G 29/22; C10G 29/205; C10G 2/331; C10G 2400/30; C07C 6/126; C07C 5/2732; C07C 1/0485; C07C 1/0425; C07C 2/864; C07C 2529/40
See application file for complete search history.

(56) References Cited

U.S. PATENT DOCUMENTS

| | | |
|---|---|---|
| 3,702,886 A | 11/1972 | Argauer et al. |
| 3,709,979 A | 1/1973 | Chu |
| 3,832,449 A | 8/1974 | Rosinski et al. |
| 4,016,218 A | 4/1977 | Haag et al. |
| 4,016,245 A | 4/1977 | Plank et al. |
| 4,076,842 A | 2/1978 | Plank et al. |
| 4,117,026 A | 9/1978 | Haag et al. |
| RE29,948 E | 3/1979 | Dwyer et al. |
| 4,229,424 A | 10/1980 | Kokotailo |
| 4,234,231 A | 11/1980 | Yan |
| 4,356,338 A | 10/1982 | Young |
| 4,439,409 A | 3/1984 | Puppe et al. |
| 4,556,477 A | 12/1985 | Dwyer |
| 4,826,667 A | 5/1989 | Zones et al. |
| 4,954,325 A | 9/1990 | Rubin et al. |
| 5,110,776 A | 5/1992 | Chitnis et al. |
| 5,231,064 A | 7/1993 | Absil et al. |
| 5,236,575 A | 8/1993 | Bennett et al. |
| 5,250,277 A | 10/1993 | Kresge et al. |
| 5,348,643 A | 9/1994 | Absil et al. |

(Continued)

FOREIGN PATENT DOCUMENTS

| | | |
|---|---|---|
| EP | 0293032 | 11/1988 |
| WO | 97/17290 | 5/1997 |

OTHER PUBLICATIONS

Ge, S., He, D., & Li, Z. (2008). A Mesoporous Ce0.5Zr0.5O2 Solid Solution Catalyst for CO Hydrogenation to iso-C4 Hydrocarbons. Catalysis letters, 126(1-2), 193-199.*

(Continued)

*Primary Examiner* — In Suk Bullock
*Assistant Examiner* — Youngsul Jeong

(57) ABSTRACT

This disclosure relates to the production of xylenes from syngas, in which the syngas is converted to an aromatic product by reaction with an isosynthesis catalyst and an aromatization catalyst. The isosynthesis catalyst and aromatization catalyst may be different catalysts or combined into a single catalyst. The aromatic product is then subjected to one of more of (i) xylene isomerization, (ii) transalkylation with at least one $C_9$+ aromatic hydrocarbon, and (iii) alkylation with methanol and/or carbon monoxide and hydrogen to increase its p-xylene content.

14 Claims, No Drawings

(56) References Cited

U.S. PATENT DOCUMENTS

| | | | |
|---|---|---|---|
| 5,362,697 | A | 11/1994 | Fung et al. |
| 5,476,823 | A | 12/1995 | Beck et al. |
| 5,895,828 | A * | 4/1999 | Yao ................. C10G 45/64 208/135 |
| 6,077,498 | A | 6/2000 | Diaz Cabanas et al. |
| 6,245,219 | B1 | 6/2001 | Kao |
| 6,459,006 | B1 | 10/2002 | Ou et al. |
| 7,663,010 | B2 * | 2/2010 | Levin ................. C07C 6/126 585/470 |
| 7,772,447 | B2 * | 8/2010 | Iaccino ................. C07C 2/76 585/320 |
| 2005/0107481 | A1 | 5/2005 | Janssen et al. |
| 2007/0259972 | A1 | 11/2007 | Lattner et al. |
| 2008/0033218 | A1 | 2/2008 | Lattner et al. |
| 2010/0144907 | A1 | 6/2010 | Kibby et al. |
| 2011/0263918 | A1 * | 10/2011 | Ou ................. B01J 29/40 585/481 |
| 2011/0319688 | A1 | 12/2011 | Ou |
| 2013/0253245 | A1 * | 9/2013 | Zheng ................. C07C 2/865 585/467 |
| 2013/0303814 | A1 | 11/2013 | Mammadov et al. |
| 2014/0171691 | A1 * | 6/2014 | Kortan ................. C07C 41/00 568/698 |
| 2015/0158792 | A1 | 6/2015 | Keusenkothen et al. |

OTHER PUBLICATIONS

Guisnet, Michel, and Jean-Pierre Gilson, eds. Zeolites for cleaner technologies. vol. 3. World Scientific, 2002.*

NETL, Gasification Introduction, Syngas Composition. Accessed Sep. 22, 2016 at https://www.netl.doe.gov/research/coal/energysystems/gasification/gasifipedia/syngascomposition.*

Bhatia, S. (1989). Zeolite catalysts: principles and applications. CRC press. p. 94.*

Silla, H. Chemical process engineering: design and economics. CRC Press, 2003.*

Dagle, R. A., Lizarazo-Adarme, J. A., Dagle, V. L., Gray, M. J., White, J. F., King, D. L., & Palo, D. R. (2014). Syngas conversion to gasoline-range hydrocarbons over Pd/ZnO/Al$_2$O$_3$ and ZSM-5 composite catalyst system. Fuel Processing Technology, 123, 65-74.*

L.A. Bruce et al. "Conversion of synthesis gas to aromatic-containing hydrocarbons under mild conditions", Applied Catalsis, vol. 0, No. 3, Mar. 1984, pp. 351-359.

R.L. Varma et al. "Direct conversion of synthesis gas to aromatic hydrocarbons: Variation of product distribution with time-on-stream", The Canadian Journal of Chemical Engineering, vol. 64, No. 1, Feb. 1986, pp. 141-148.

N. Guan et al "Development of catalysts for the production of aromatics from syngas", Catalysis Today, vol. 30, No. 1-3, Jun. 1996, pp. 207-213.

Yoshio, Ono et al. "Selective conversion of methanol into aromatic hydrocarbons over zinc-exchanged ZSM-5 zeolites", Journal of the Chemical Society, Faraday Transactions 1, vol. 84, No. 4, Jan. 1988, p. 1091.

Wang Desheng et al., "Direct Conversion of Syngas into Aromatics over Bifunctional Fe/MnO—ZnZSM-5 Catalyst", Chinese Journal of Catalysis, vol. 23, No. 4 Jul. 2002.

Chemical and Engineering News, 63(5), 27 (1985).

Ge, et al., Catal. Lett 2008, 126, pp. 193-197.

* cited by examiner

PRODUCTION OF XYLENES FROM SYNGAS

PRIORITY CLAIM

This application claims priority to and the benefit of U.S. Provisional Application No. 62/028,486, filed Jul. 24, 2014 which is incorporated by reference in its entirety.

FIELD

This disclosure relates to the production of xylenes from syngas.

BACKGROUND

The isomers of xylene find wide and varied application. For example, meta-xylene (m-xylene) is used in the manufacture of dyes, and ortho-xylene (o-xylene) is used as a feedstock for producing phthalic anhydride, which finds use in the manufacture of plasticizers. However, currently the most valuable of the xylene isomers is para-xylene (p-xylene), since p-xylene is a feedstock for terephthalic acid, which in turn is used in the manufacture of polyester fibers and films.

The majority of p-xylene produced today is derived from crude oil via reforming of the naphtha portion of the crude into a mixture of benzene, toluene, and xylenes (BTX) and heavier aromatics. These aromatics then undergo a variety of reactions, such as transalkylation, disproportionation, and xylene isomerization, to increase the concentration of p-xylene. The current commercial process also requires extraction of aromatics from non-aromatics and separation of p-xylene from a mixture of xylene isomers via crystallization or molecular sieve adsorption. The overall process is therefore complex. Moreover, as crude oil prices rise, so does the feed stock price for p-xylene production via the current commercial routes. Recently, as crude prices have risen, the prices of coal and natural gas having fallen making syngas derived from these sources cheaper on a carbon or energy equivalent basis and a potentially attractive feed for the production of basic chemicals, such as p-xylene.

The conversion of syngas to olefins and paraffins has been widely practiced for many years via the Fischer-Tropsch process and indirectly via the methanol to olefins (MTO) process. However, both of these syngas conversion routes produce only small amounts of aromatics and there is therefore a need for an improved route for converting syngas to aromatics, and particularly, p-xylene.

In a paper entitled "Direct Conversion of Syngas into Aromatics over Bifunctional Fe/MnO—ZnZSM-5 Catalyst", Chinese Journal of Catalysis, Volume 23, No. 4 July, 2002, Wang Desheng et al. report that syngas can be converted into aromatics at high yield using a bifunctional catalyst comprising Fe/MnO mixed with Zn-ZSM-5 containing up to 7 wt % Zn under conditions including a temperature of 517° F. (270° C.), a pressure of 160 psig, and a hydrogen to carbon monoxide molar ratio of 2:1. However, the aromatic product slate obtained in the process of Wang et al. is composed mainly of benzene and toluene, rather than the more desirable p-xylene. Further, the preferred operating conditions of the Fischer-Tropsch process and aromatization process differ, limiting the conversion and selectivity to aromatics.

Another method for the conversion of syngas to higher hydrocarbons is isosynthesis, in which syngas is converted to $C_4$ hydrocarbons. Because the isosynthesis reaction occurs in the same preferred temperature range as the aromatization reaction, there is a desire to combine isosynthesis with aromatization to provide a process of converting syngas to aromatics in which the yield of xylene isomers, and in particular p-xylene, is improved.

SUMMARY

The present invention is directed to the conversion of syngas over a combination of an isosynthesis catalyst and an aromatization catalyst to effectively and cost efficiently produce a BTX-containing mixture which can then be subjected to isomerization, transalkylation and/or methylation to increase the para-xylene content of the mixture. A first feed comprising hydrogen and carbon monoxide in a molar ratio of hydrogen to carbon monoxide from about 0.5 to 6 is contacted with (i) a first catalyst comprising at least one metal or compound containing a metal selected from the group consisting of Ce, Zn, Zr, and Th, and (ii) a second catalyst, which may be the same as or different than the first catalyst, comprising at least one medium pore size molecular sieve under conditions including a temperature of at least 350° C. and a pressure of at least 1500 kPa (absolute) effective to produce a reaction effluent containing benzene, toluene, and xylenes. In some embodiments, xylenes, especially p-xylene, are recovered directly from the reaction effluent. In other embodiments, at least part of the reaction effluent is subsequently subjected to at least one of (a) contacting with a xylene isomerization catalyst, (b) transalkylation with at least one $C_9+$ aromatic hydrocarbon, and (c) alkylation with methanol and/or carbon monoxide and hydrogen to increase the xylene concentration of the effluent.

The invention further provides a catalyst system comprising a first catalyst comprising at least one metal or compound containing a metal selected from the group consisting of Ce, Zn, Zr, and Th, and a second catalyst, which may be the same as or different than the first catalyst, comprising at least one molecular sieve and at least one metal from Groups 10-14 of the Periodic Table or compound thereof, with the first and second catalysts located within the same reactor bed.

DETAILED DESCRIPTION

The present disclosure relates to a process for the production of xylenes, and particularly p-xylene, from syngas. The initial syngas conversion proceeds via an isosynthesis catalyst and an aromatization catalyst, which may be different catalysts or combined into a single catalyst, to produce a hydrocarbon mixture containing benzene, toluene, and xylenes (BTX). P-xylene can then be recovered directly from the BTX product and/or at least part of the BTX can be subjected to alkylation, transalkylation and/or isomerization processes to enhance the p-xylene concentration of the product.

Definitions

For the purpose of this specification and appended claims, the following terms are defined. The term "$C_n$" hydrocarbon wherein n is a positive integer, e.g., 1, 2, 3, 4, or 5, means a hydrocarbon having n number of carbon atom(s) per molecule. The term "$C_{n+}$" hydrocarbon wherein n is a positive integer, e.g., 1, 2, 3, 4, or 5, means hydrocarbon having at least n number of carbon atom(s) per molecule. The term "$C_{n-}$" hydrocarbon wherein n is a positive integer, e.g., 1, 2, 3, 4, or 5, means hydrocarbon having no more than n number of carbon atom(s) per molecule. The term "aromatics" means hydrocarbon molecules containing at least one aromatic core. The term "hydrocarbon" encompasses mixtures of hydrocarbon, including those having different values of n. The term "syngas" means a gaseous mixture comprising hydrogen, carbon monoxide, and optionally some carbon dioxide.

As used herein, the numbering scheme for the groups of the Periodic Table of the Elements is as disclosed in Chemical and Engineering News, 63(5), 27 (1985).

Syngas-Containing Feed

The syngas-containing feed employed in the present process comprises hydrogen and at least 4 mol. %, for example at least 10 mol. %, of carbon monoxide, such that the molar ratio of hydrogen to carbon monoxide in the feed is from about 0.5 to 20, preferably from about 0.5 to 10, more preferably from about 0.6 to 6 or from about 0.8 to 4, and most preferably from about 1 to 3. In a preferred embodiment, the molar ratio of hydrogen to carbon monoxide is from about 0.5 to 6. The syngas may also contain carbon dioxide such that the feed can have a $H_2$: $(CO+CO_2)$ molar ratio of from 2 to 60.

The syngas can be produced from methane and/or other carbon-containing source material. The type of carbon-containing source material used is not critical. The source material can comprise, e.g., methane and other lower ($C_{4-}$) alkanes, such as contained in a natural gas stream, or heavier hydrocarbonaceous materials, such as coal and biomass. Desirably, the source material comprises ≥10 vol. %, such as ≥50 vol. %, based on the volume of the source material, of at least one hydrocarbon, especially methane.

The source material can be converted to syngas by any convenient method, including those well-established in the art. Suitable methods include those described in U.S. Patent Application Publication Nos. 2007/0259972 A1, 2008/0033218 A1, and 2005/0107481 A1, each of which is incorporated by reference herein in its entirety.

For example, natural gas can be converted to syngas by steam reforming. This normally involves the initial removal of inert components in the natural gas, such as nitrogen, argon, and carbon dioxide. Natural gas liquids can also be recovered and directed to other processing or transport. The purified natural gas is then contacted with steam in the presence of a catalyst, such as one or more metals or compounds thereof selected from Groups 7 to 10 of the Periodic Table of the Elements supported on an attrition resistant refractory support, such as alumina. The contacting is normally conducted at high temperature, such as in the range of from 800° C. to 1100° C., and pressures ≤5000 kPa. Under these conditions, methane converts to carbon monoxide and hydrogen according to reactions such as:

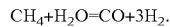
$$CH_4+H_2O=CO+3H_2.$$

Steam reforming is energy intensive in that the process consumes over 200 kJ/mole of methane consumed. A second method of producing syngas from methane is partial oxidation, in which the methane is burned in an oxygen-lean environment. The methane is partially-oxidized to carbon monoxide (reaction (i)), with a portion of the carbon monoxide being exposed to steam reforming conditions (reaction (ii)) to produce molecular hydrogen and carbon dioxide, according to the following representative reactions:

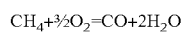
$$CH_4+\tfrac{1}{2}O_2=CO+2H_2O \qquad (i),$$

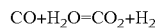
$$CO+H_2O=CO_2+H_2 \qquad (ii).$$

Partial oxidation is exothermic and yields a significant amount of heat. Because steam reforming reaction is endothermic and partial oxidation is exothermic, these two processes are often performed together for efficient energy usage. Combining the steam reforming and partial oxidation yields a third process for generating syngas from natural gas in which the heat generated by partial oxidation is used to drive steam reforming to yield syngas.

In certain embodiments, especially those employing an isosynthesis catalyst for the initial syngas conversion, the syngas-containing feed can also contain one or more $C_4$-hydrocarbons, especially methane, present either as unreacted reagent from natural gas used to produce the syngas feed or added deliberately to the syngas feed. Thus, although methane may be unreactive with the isosynthesis catalyst under the typical conditions employed in the syngas conversion process, methane will co-react with iso-$C_4$ hydrocarbons during aromatization to incorporate —$CH_x$— groups into the aromatic rings and reduce $C_2$+ hydrocarbon cracking. In embodiments where methane is present or added to the syngas-containing feed, the molar ratio of methane to CO in the feed may be from 25 to 1, such as from 10 to 3.

Production of BTX from Syngas Via Isosynthesis/Aromatization

In certain aspects, the present disclosure provides a process for converting syngas to a product mixture comprising benzene, toluene, and xylenes (BTX) by a combination of an isosynthesis reaction and an aromatization reaction. Para-xylene can be recovered from the BTX-containing product either directly or after post-treatment of the product by one of more of (a) xylene isomerization, (b) transalkylation with at least one $C_9$+ aromatic hydrocarbon, and (c) para-selective methylation to increase the para-xylene concentration of the product.

Isosynthesis is a process for converting synthesis gas to a product containing $C_4$+ hydrocarbons, primarily branched aliphatic $C_{4+}$ hydrocarbons, at relatively high temperatures and pressures. The present process may be conducted over a first catalyst with an isosynthesis functionality comprising at least one metal or compound thereof selected from Ce, Zn, Zr, and Th. The isosynthesis catalyst may comprise a single active metallic species or may comprise a multimetallic, such as a bimetallic or trimetallic, composition. For example, in one embodiment the isosynthesis catalyst may comprise a combination of Ce and Zr, either in metallic or oxide form or a combination thereof. The amount of active metallic species present in the isosynthesis catalyst can vary widely depending on the particular metal or metals present in the catalyst. For example, where the isosynthesis catalyst comprises a combination of Ce and Zr, the catalyst can contain from 0.1 to 10 Ce/Zr mol ratio; such as from 0.5 to 2 Ce/Zr mol ratio. In one embodiment, the isosynthesis catalyst comprises a mixed oxide of Ce and Zr having the general formula $Ce_{0.5}Zr_{0.5}O_2$.

The active metallic species of the isosynthesis catalyst may be self-supporting or may be loaded on one or more supports selected from, for example, zinc oxide, magnesium oxide, alumina, silica, carbon, and mixtures thereof. Suitable carbon supports include activated carbon, carbon black, carbon nanotubes, and carbon nanofibers. In certain embodiments, the isosynthesis catalyst may further comprise one or more elements selected from Groups 1 to 4 of the Periodic Table, such as Cs, K, and/or Ca, or compounds thereof, to act as stabilizers for the active metallic species of the catalyst.

The present isosynthesis reaction comprises contacting a syngas-containing feed, as described above, optionally in the presence of added methane, with a first catalyst with an isosynthesis functionality as described above under conditions including a temperature of least 350° C. and a pressure of least 1,500 kPa (absolute). Thus, in certain embodiments, the isosynthesis reaction is conducted at a temperature from 350° C. to 650° C. and a pressure from 1,500 to 13,000 kPa (absolute), preferably a temperature from 450° C. to 600° C. and a pressure from 2,000 to 7,000 kPa (absolute), and more preferably a temperature from 500° C. to 550° C. and a pressure from 2,500 to 5,000 kPa (absolute).

In the present process, the product of the isosynthesis reaction is contacted with a second catalyst with an aromatization functionality comprising at least one molecular sieve and optionally at least one dehydrogenation component. The second catalyst comprises at least one molecular sieve and, in certain aspects, at least one medium pore size molecular sieve having a Constraint Index of 2-12 (as defined in U.S. Pat. No. 4,016,218). Examples of such medium pore molecular sieves include ZSM-5, ZSM-11, ZSM-12, ZSM-22, ZSM-23, ZSM-35, ZSM-48, and mixtures and intermediates thereof. ZSM-5 is described in detail in U.S. Pat. No. 3,702,886 and Re. 29,948. ZSM-11 is described in detail in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

In other aspects, the second catalyst employed in the present process comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as a molecular sieve component of the present catalyst.

In certain aspects, the molecular sieve employed in the aromatization catalyst may be an aluminosilicate or a substituted aluminosilicate in which part of all of the aluminum is replaced by a different trivalent metal, such as gallium or indium.

In addition to the molecular sieve component, the aromatization catalyst may comprise at least one dehydrogenation component, e.g., at least one dehydrogenation metal. The dehydrogenation component is typically present in an amount of at least 0.1 wt %, such as from 0.1 to 10 wt %, of the overall catalyst. The dehydrogenation component can comprise one or more neutral metals selected from Groups 3 to 13 of the Periodic Table of the Elements, such as Ga, In, Zn, Cu, Re, Mo, W, La, Fe, Ag, Pt, Pd, Ni, and/or one or more oxides, sulfides and/or carbides of these metals. The dehydrogenation component can be provided on the catalyst in any manner, for example by conventional methods such as impregnation or ion exchange of the molecular sieve with a solution of a compound of the relevant metal, followed by conversion of the metal compound to the desired form, namely neutral metal, oxide, sulfide, and/or carbide. Part or all of the dehydrogenation metal may also be present in the crystalline framework of the molecular sieve.

In one embodiment, the aromatization catalyst comprises ZSM-5 containing from 0.1 to 10 wt % Zn.

In some embodiments, the aromatization catalyst is selectivated, either before introduction into the aromatization reactor or in-situ in the reactor, by contacting the catalyst with a selectivating agent. In one embodiment, the catalyst is silica-selectivated by contacting the catalyst with at least one organosilicon in a liquid carrier and subsequently calcining the silicon-containing catalyst in an oxygen-containing atmosphere, e.g., air, at a temperature of 350° C. to 550° C. A suitable silica-selectivation procedure is described in U.S. Pat. No. 5,476,823, the entire contents of which are incorporated herein by reference. In another embodiment, the catalyst is selectivated by contacting the catalyst with steam. Steaming of the zeolite is effected at a temperature of at least about 950° C., preferably about 950° C. to about 1075° C., and most preferably about 1000° C. to about 1050° C. for about 10 minutes to about 10 hours, preferably from 30 minutes to 5 hours. The selectivation procedure, which may be repeated multiple times, alters the diffusion characteristics of the catalyst and may increase the xylene yield during the aromatization process.

In addition to, or in place of, silica or steam selectivation, the catalyst may be subjected to coke selectivation. This optional coke selectivation typically involves contacting the catalyst with a thermally decomposable organic compound at an elevated temperature in excess of the decomposition temperature of said compound but below the temperature at which the crystallinity of the molecular sieve is adversely affected. Further details regarding coke selectivation techniques are provided in the U.S. Pat. No. 4,117,026, incorporated by reference herein. In some embodiments, a combination of silica selectivation and coke selectivation may be employed.

Aromatization of the isosynthesis reaction product may be conducted over a wide range of temperature and pressures, although generally temperatures of least 350° C. are desirable. Thus, in certain embodiments, the aromatization reaction is conducted at a temperature from 350° C. to 600° C. and a pressure from 1,500 to 10,000 kPa (absolute), for example at a temperature from 375° C. to 500° C. and a pressure from 2000 to 7000 kPa (absolute). Desirably, the isosynthesis reaction and the aromatization reaction are conducted under substantially the same conditions.

The isosynthesis reaction and the aromatization reaction may be conducted in separate catalyst beds arranged in series or the same reaction vessel. Alternatively, the isosynthesis reaction and the aromatization reaction may be conducted in the same reaction bed with the catalysts being stacked, mixed or combined into a single multi-functional catalyst particle. In such a case, it will be appreciated the iso-$C_{4+}$ containing hydrocarbon product of the isosynthesis reaction may be instantaneously converted by the aromatization catalyst into a heavier aromatic-containing product.

Where the isosynthesis and aromatization reactions are conducted in separate catalyst beds, the effluent from the isosynthesis reaction can be subjected to one or more separation steps to remove unreacted components, such as unreacted syngas, and reaction by-products, such as water, $CO_2$ and $H_2$, before the iso-$C_{4+}$ containing hydrocarbon product is forwarded to the aromatization reaction. Optionally, the unreacted syngas is recycled to the isosynthesis reaction.

The effluent from the aromatization reaction comprises a $C_5$+ hydrocarbon product together with water, $CO_2$, $H_2$, and small quantities of $C_{4-}$ hydrocarbons. In certain embodiments, the $C_{5+}$ hydrocarbon product comprises from 1 to 50 wt % aromatics. The aromatization effluent can be subjected to one or more separation processes to remove unwanted by-products, such as water and $CO_2$, and to recover $H_2$, which can be recycled to the isosynthesis reaction, and $C_{5-}$ hydrocarbons, which can be used as fuel. At least part of the aromatic product in the effluent is then subjected to one or more post-treatments to increase the concentration of paraxylene. Suitable post treatments include at least one of (a) contacting with a xylene isomerization catalyst, (b) transalkylation with at least one $C_9$+ aromatic hydrocarbon, and (c) para-selective alkylation with methanol and/or carbon monoxide and hydrogen.

Where the at least one of post-treatment comprises contacting at least part of the aromatic product in the effluent with a xylene isomerization catalyst, the benzene and toluene components and any $C_{9+}$ components in the aromatization effluent may initially be removed, for example by distillation, to produce a $C_8$-containing fraction. The $C_8$-containing fraction can then be fed to p-xylene separation section, where p-xylene is recovered by adsorption or crystallization or a combination of both and the residual p-xylene-depleted stream contacted with any known xylene isomerization catalyst system operating in either the vapor phase or liquid phase. A suitable xylene isomerization catalyst system comprises the liquid phase process described in U.S. Patent Application Publication Nos. 2011/0263918 and 2011/0319688, the entire contents of each of which are incorporated herein by reference. Such a process employs a molecular sieve xylene isomerization catalyst, such as ZSM-5 or MCM-49, and operates at a temperature from 230° C. to 300° C., a pressure from about 1300 to about 2100 kPa (absolute) and a weight hourly space velocity (WHSV) of from about 0.5 to about 10 $hr^{-1}$ to convert the p-xylene-depleted stream back or close to equilibrium xylenes concentration with very low by-product formation. The isomerized product can then be recycled to p-xylene separation section for further recovery of p-xylene, while the benzene, toluene components and any $C_{9+}$ components removed from the aromatization effluent can be fed to the transalkylation process described below.

Where the at least one of post-treatment comprises transalkylation of at least part of the aromatic product in the effluent with at least one $C_9$+ aromatic hydrocarbon, a $C_8$-containing fraction may initially be removed from the aromatization effluent, for example by distillation, and supplied to the xylene recovery and isomerization process discussed above. The remainder of the aromatization effluent, containing benzene and toluene, is then supplied to a transalkylation process together with at least one $C_{9+}$ aromatic hydrocarbon, generally from an external source. Any transalkylation process known to those skilled in the art can be used, but one preferred process employs the multi-stage catalytic system described in U.S. Pat. No. 7,663,010, incorporated herein by reference in its entirety. Such a system comprises (i) a first catalyst comprising a first molecular sieve having a Constraint Index in the range of 3-12 and containing 0.01 to 5 wt % of at least one source of a first metal element of Groups 6-10 of the Periodic Table and (ii). a second catalyst comprising a second molecular sieve having a Constraint Index less than 3 and comprising 0 to 5 wt % of at least one source of a second metal element of Groups 6-10 of the Periodic Table, wherein the weight ratio of the first catalyst for the second catalyst is in the range of 5:95 to 75:25 and wherein the first catalyst is located upstream of the second catalyst.

Examples of suitable molecular sieves having a Constraint Index of 3-12 for use in the first catalyst include ZSM-5, ZSM-11, ZSM-22, ZSM-23, ZSM-35, ZSM-48, ZSM-57 and ZSM-58, with ZSM-5 being preferred. Examples of suitable molecular sieves having a Constraint Index of less than 3 for use in the second catalyst include zeolite beta, zeolite Y, Ultrastable Y (USY), Dealuminized Y (Deal Y), mordenite, ZSM-3, ZSM-4, ZSM-12, ZSM-18, NU-87 and ZSM-20, with ZSM-12 being preferred. Specific examples of useful metals for each of the first and second catalysts include iron, ruthenium, osmium, nickel, cobalt, rhodium, iridium, and noble metals such as platinum or palladium.

The transalkylation process can be conducted in any appropriate reactor including a radial flow, fixed bed, continuous down flow, or fluid bed reactor. The conditions in the first and second catalyst bed can be the same or different but generally comprise a temperature from 100° C. to 1000° C., preferably in the range of 300° C. to 500° C.; a pressure in the range of 790 to 7000 kPa-a (kilo-Pascal absolute), preferably in the range of 2170 to 3000 kPa-a, a hydrogen to hydrocarbon molar ratio from 0.01 to 20, preferably from 1 to 10; and a WHSV from 0.01 to 100 $hr^{-1}$, preferably in the range of 1-20 $hr^{-1}$.

Where the at least one of post-treatment comprises para-selective alkylation of at least part of the aromatic product in the effluent with methanol and/or carbon monoxide and hydrogen, a $C_{8+}$-containing fraction may initially be removed from the aromatization effluent, for example by distillation, and supplied to the xylene recovery and isomerization process discussed above. The remainder of the aromatization effluent, containing benzene and toluene, is then supplied to a para-selective alkylation.

In certain aspects, methylation of the benzene and toluene in the aromatization effluent is conducted over an alkylation catalyst comprising a molecular sieve having a Diffusion Parameter for 2,2-dimethylbutane of about 0.1-15 $sec^{-1}$, such as 0.5-10 $sec^{-1}$, when measured at a temperature of 120° C. and a 2,2-dimethylbutane pressure of 60 torr (8 kPa). As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The molecular sieve employed in the present alkylation process is normally a medium-pore size aluminosilicate zeolite. Medium pore zeolites are generally defined as those having a pore size of about 5 to about 7 Angstroms, such that the zeolite freely sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

The medium pore zeolites described above are particularly effective for the present alkylation process since the size and shape of their pores favor the production of p-xylene over the other xylene isomers. However, conventional forms of these zeolites have Diffusion Parameter values in excess of the 0.1-15 sec$^{-1}$ range referred to above. However, the required diffusivity for the catalyst can be achieved by severely steaming the catalyst so as to effect a controlled reduction in the micropore volume of the catalyst to not less than 50%, and preferably 50-90%, of that of the unsteamed catalyst. Reduction in micropore volume is derived by measuring the n-hexane adsorption capacity of the catalyst, before and after steaming, at 90° C. and 75 torr n-hexane pressure.

Steaming of the zeolite is effected at a temperature of at least about 950° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the zeolite, prior to steaming, with at least one oxide modifier, such as at least one oxide selected from elements of Groups 2 to 4 and 13 to 16 of the Periodic Table. Preferably, said at least one oxide modifier is selected from oxides of boron, magnesium, calcium, lanthanum, and more preferably, phosphorus. In some cases, the zeolite may be combined with more than one oxide modifier, for example a combination of phosphorus with calcium and/or magnesium, since in this way it may be possible to reduce the steaming severity needed to achieve a target diffusivity value. In some embodiments, the total amount of oxide modifier present in the catalyst, as measured on an elemental basis, may be between about 0.05 and about 20 wt %, and preferably is between about 0.1 and about 10 wt %, based on the weight of the final catalyst.

Where the modifier includes phosphorus, incorporation of modifier into the catalyst is conveniently achieved by the methods described in U.S. Pat. Nos. 4,356,338; 5,110,776; 5,231,064; and 5,348,643, the entire disclosures of which are incorporated herein by reference. Treatment with phosphorus-containing compounds can readily be accomplished by contacting the zeolite, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt %. Suitable phosphorus compounds include, but are not limited to, phosphonic, phosphinous, phosphorus and phosphoric acids, salts and esters of such acids, and phosphorous halides.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150° C. to 750° C., preferably about 300° C. to 500° C., for at least 1 hour, preferably 3-5 hours. Similar techniques known in the art can be used to incorporate other modifying oxides into the catalyst employed in the alkylation process.

In addition to the zeolite and modifying oxide, the catalyst employed in the alkylation process may include one or more binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such assilica-alumina-thoria, silica-alumina-zirconia, silica-alumina-magnesia, and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt % of the composite. Preferably, the matrix material comprises silica or a kaolin clay.

The alkylation catalyst used in the present process may optionally be precoked. The precoking step is may be carried out by initially loading uncoked catalyst into the methylation reactor. Then, as the reaction proceeds, coke is deposited on the catalyst surface and thereafter may be controlled within a desired range, typically from about 1 to about 20 wt % and preferably from about 1 to about 5 wt %, by periodic regeneration by exposure to an oxygen-containing atmosphere at an elevated temperature.

In certain aspects, methylation of the benzene and toluene in the aromatization effluent is effected with a methylating agent comprising methanol and/or a mixture of carbon monoxide and hydrogen. In the latter case, the molar ratio of carbon monoxide to hydrogen in the methylating agent may comprise from 1 to 4, such as from 1.5 to 3.0. Suitable conditions for the methylation reaction a temperature from 350° C. to 700° C., preferably from 500° C. to 600° C., a pressure of from 100 and 7000 kPa absolute, a weight hourly space velocity of from 0.5 to 1000 hr$^{-1}$, and a molar ratio of toluene to methanol (in the reactor charge) of at least about 0.2, e.g., from about 0.2 to about 20. The process may suitably be carried out in fixed, moving, or fluid catalyst beds. If it is desired to continuously control the extent of coke loading, moving or fluid bed configurations are preferred. With moving or fluid bed configurations, the extent of coke loading can be controlled by varying the severity and/or the frequency of continuous oxidative regeneration in the catalyst regenerator.

Using the present process, toluene can be alkylated with methanol so as to produce para-xylene at a selectivity of at least about 80 wt % (based on total $C_8$ aromatic product) at a per-pass aromatic conversion of at least about 15 wt % and a trimethylbenzene production level less than 1 wt %. Unreacted benzene and toluene and methylating agent and a portion of the water by-product may be recycled to the methylation reactor and heavy byproducts routed to fuels dispositions. The C8 fraction is routed to a para-xylene recovery unit, which typically operates by fractional crystallization or by selective adsorption (e.g. Parex or Eluxyl) to recover a para-xylene product stream from the alkylation effluent and leave a para-xylene-depleted stream containing mainly $C_7$ and $C_8$ hydrocarbons. The para-xylene-depleted stream may be isomerized and recycled to the para-xylene recovery unit.

The description above support one or more of the following more specific Embodiments.

Embodiment 1

A process for producing xylenes, the process comprising: (a) providing a feed comprising hydrogen and carbon monoxide, in which the molar ratio of hydrogen to carbon monoxide is from 0.5 to 6; (b) contacting the feed with (i) a first catalyst comprising at least one metal or compound containing a metal selected from the group consisting of Ce, Zn, Zr, and Th, and (ii) a second catalyst, which may be the same as or different than the first catalyst, comprising at least one medium pore size molecular sieve under conditions including a temperature of at least 350° C. and a pressure of at least 1500 kPa (absolute) effective to produce a reaction effluent containing benzene, toluene, and xylenes; and (c) subjecting at least part of the reaction effluent to at least one of (i) contacting with a xylene isomerization catalyst, (ii) transalkylation with at least one $C_9+$ aromatic hydrocarbon, and (iii) alkylation with methanol and/or carbon monoxide and hydrogen under conditions to produce p-xylene.

Embodiment 2

The process of Embodiment 1, wherein the feed further comprises methane.

Embodiment 3

The process of Embodiment 1 or Embodiment 2, wherein the first catalyst comprises $Ce_{0.5}Zr_{0.5}O_2$.

Embodiment 4

The process of any one of Embodiments 1 to 3, wherein the second catalyst comprises at least one molecular sieve having a Constraint Index of 1-12.

Embodiment 5

The process of any one of Embodiments 1 to 4, wherein the at least one molecular sieve of the second catalyst comprises ZSM-5.

Embodiment 6

The process of any one of Embodiments 1 to 5, wherein the second catalyst comprises at least one metal or compound thereof, wherein the metal is selected from the group consisting of Ga, In, Zn, Cu, Re, Mo, W, La, Fe, Ag, Pt, Pd, and Ni.

Embodiment 7

The process of any one of Embodiments 1 to 6, wherein the second catalyst is silica-selectivated.

Embodiment 8

The process of any one of Embodiments 1 to 7, wherein the second catalyst is steam-selectivated.

Embodiment 9

The process of any one of Embodiments 1 to 8, wherein the first and second catalysts are located in different reaction beds.

Embodiment 10

The process of any one of Embodiments 1 to 9, wherein the first and second catalysts are different but are located in the same reaction bed.

Embodiment 11

The process of any one of Embodiments 1 to 9, wherein the first and second catalysts are combined into a single multi-functional catalyst.

Embodiment 12

The process of any one of Embodiments 1 to 11, wherein the conditions in (b) comprise a temperature from 350 to 600° C. and a pressure from 1,500 to 10,000 kPa (absolute).

Embodiment 13

The process of any one of Embodiments 1 to 12, wherein (c) comprises contacting at least part of the xylenes in the reaction effluent with xylene isomerization catalyst.

Embodiment 14

The process of any one of Embodiments 1 to 12, wherein (c) comprises transalkylating at least part of the benzene and/or toluene in the reaction effluent with at least one $C_9+$ aromatic hydrocarbon.

Embodiment 15

The process of any one of Embodiments 1 to 12, wherein (c) comprises alkylating at least part of the benzene and/or toluene in the reaction effluent with methanol and/or hydrogen and carbon monoxide in the presence of a third catalyst comprising at least one molecular sieve having a Diffusion Parameter for 2,2-dimethylbutane of from 0.1 to 15 $sec^{-1}$ when measured at a temperature of 120° C. and a 2,2-dimethylbutane pressure of 60 torr (8 kPa).

Embodiment 16

A catalyst system for the production of para-xylene comprising: (a) a first catalyst comprising at least one metal or compound containing a metal selected from the group consisting of Ce, Zn, Zr, and Th, and (b) a second catalyst, which may be the same as or different than the first catalyst, comprising at least one medium pore size molecular sieve and at least one metal selected from Groups 10-14 of the Periodic Table or compound thereof, wherein the first and second catalysts are located within the same reactor bed.

Embodiment 17

The catalyst system of Embodiment 16 wherein the first and second catalysts are different and are physically mixed in the same reactor bed.

Embodiment 18

The catalyst system of Embodiment 16 wherein the first and second catalysts are combined into a single multi-functional catalyst.

Embodiment 19

The catalyst system of any one of Embodiments 16-18, wherein the second catalyst comprises at least one metal or compound thereof, wherein the metal is selected from the group consisting of Ga, In, Zn, Cu, Re, Mo, W, La, Fe, Ag, Pt, Pd, and Ni.

Embodiment 20

The catalyst system of any one of Embodiments 16-19, wherein the metal of the second catalyst is present in an amount of about 0.1 to 10 wt %.

Embodiment 21

The catalyst system of any one of Embodiments 16-20, wherein the second catalyst comprises silica-selectivated ZSM-5.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated, and are expressly within the scope of the invention. The term "comprising" is synonymous with the term "including". Likewise whenever a composition, an element or a group of components is preceded with the transitional phrase "comprising", it is understood that we also contemplate the same composition or group of components with transitional phrases "consisting essentially of," "consisting of", "selected from the group consisting of," or "is" preceding the recitation of the composition, component, or components, and vice versa.

The invention claimed is:

1. A process for producing xylenes, the process comprising:
    (a) providing a feed comprising methane, hydrogen, and carbon monoxide, in which the molar ratio of hydrogen to carbon monoxide is from 0.5 to 6 and in which the molar ration of methane to carbon monoxide is from 25 to 1;
    (b) contacting the feed with (i) a first catalyst comprising at least one metal or compound containing a metal selected from the group consisting of Ce, Zn, Zr, and Th, and (ii) a second catalyst comprising at least one medium pore size molecular sieve,
    wherein the contacting in (b)(i) and (b)(ii) is carried out under conditions including a temperature of at least 350° C. and a pressure of at least 1500 kPa (absolute) effective to produce a reaction effluent containing benzene, toluene, and xylenes; and
    (c) subjecting at least part of the reaction effluent to at least one of (i) contacting with a xylene isomerization catalyst, (ii) transalkylation with at least one $C_9+$ aromatic hydrocarbon, and (iii) alkylation with methanol and/or the combination of carbon monoxide and hydrogen under conditions to produce p-xylene.

2. The process of claim 1, wherein the first catalyst comprises $Ce_{0.5}Zr_{0.5}O_2$.

3. The process of claim 1, wherein the second catalyst comprises at least one molecular sieve having a Constraint Index of 1-12.

4. The process of claim 1, wherein the at least one medium pore size molecular sieve of the second catalyst comprises ZSM-5.

5. The process of claim 1, wherein the second catalyst comprises at least one metal or compound thereof, wherein the metal is selected from the group consisting of Ga, In, Zn, Cu, Re, Mo, W, La, Fe, Ag, Pt, Pd, and Ni.

6. The process of claim 1, wherein the second catalyst is silica-selectivated.

7. The process of claim 1, wherein the second catalyst is steam-selectivated.

8. The process of claim 1, wherein the first and second catalysts are located in different reaction beds.

9. The process of claim 1, wherein the first and second catalysts are different but are located in the same reaction bed.

10. The process of claim 1, wherein the first and second catalysts are combined into a single multi-functional catalyst.

11. The process of claim 1, wherein the conditions in (b) comprise a temperature from 350 to 600° C. and a pressure from 1,500 to 10,000 kPa (absolute).

12. The process of claim 1, wherein (c) comprises contacting at least part of the xylenes in the reaction effluent with xylene isomerization catalyst.

13. The process of claim 1, wherein (c) comprises transalkylating at least part of the benzene and/or toluene in the reaction effluent with at least one $C_9+$ aromatic hydrocarbon.

14. The process of claim 1, wherein (c) comprises alkylating at least part of the benzene and/or toluene in the reaction effluent with methanol and/or hydrogen and carbon monoxide in the presence of a third catalyst comprising at least one molecular sieve having a Diffusion Parameter for 2,2-dimethylbutane of from 0.1 to 15 $sec^{-1}$ when measured at a temperature of 120° C. and a 2,2-dimethylbutane pressure of 60 torr (8 kPa).

* * * * *